United States Patent [19]

Sakakibara

[11] Patent Number: 5,201,230
[45] Date of Patent: Apr. 13, 1993

[54] APPARATUS FOR TESTING HOT-MELT ADHESION STRENGTH

[75] Inventor: Ryohei Sakakibara, Kobe, Japan

[73] Assignee: National Starch and Chemical Investment Holding Corporation, Wilmington, Del.

[21] Appl. No.: 703,954

[22] Filed: May 22, 1991

[30] Foreign Application Priority Data

May 23, 1990 [JP] Japan .................................. 2-53935
May 23, 1990 [JP] Japan .................................. 2-133340

[51] Int. Cl.[5] ........................................... G01N 3/08
[52] U.S. Cl. .................................................. 73/827
[58] Field of Search ............... 73/818, 825, 827, 831, 73/832, 834, 837, 856

[56] References Cited

U.S. PATENT DOCUMENTS

| | | | |
|---|---|---|---|
| 1,174,251 | 3/1916 | Hankins et al. | 73/825 |
| 4,893,513 | 1/1990 | Schroeder et al. | 73/827 |
| 4,957,009 | 9/1990 | McKinlay et al. | 73/842 |

FOREIGN PATENT DOCUMENTS 1307289 4/1987 U.S.S.R. ............................ 73/825

Primary Examiner—Robert Raevis

[57] ABSTRACT

With relation to a first test piece with an adhesive applied thereto, a second test piece is swiftly moved close to the contact bonding position by a movable actuator, and then the second test piece is pressed by a pressing actuator on the first test piece for contact bonding. When the both test pieces joined together are peeled from one another, a peel load is detected by a load cell via a table which is supported by the load cell and on which the test pieces are fixed. If a corrugated board is used as a test piece, it is held by a holding member consisting of a plurality of parallel needles which have been inserted from the side into the intermediate portion between one surface and another of the test piece and common frame members for securing the ends of the needles.

2 Claims, 6 Drawing Sheets

APPARATUS FOR TESTING HOT-MELT ADHESION STRENGTH

BACKGROUND OF THE INVENTION

The present invention relates to an apparatus for testing the adhesion strength of a hot-melt adhesive for use in adhesion between corrugated boards.

With a conventional apparatus for testing hot-melt adhesion strength, a testing process comprises steps of applying a predetermined amount of adhesives to one test piece, pressing said one test piece on other test piece with an actuator such as air cylinders into close contact therewith after a determined period of time, and peeling the one test piece from the other test piece after the passage of a period of time so that the adhesion strength of the hold-melt adhesive may be determined in view of the resultant tensile force. During said process, the test piece is held by gripping one end of the test piece by means of a clamp.

For sticking a first test piece with an adhesive applied thereto on a second test piece, said conventional apparatus for test of adhesion strength is designed to perform both operations of bringing the test pieces toward each other and putting them into close contact with each other in one procedure step using one and the same air cylinder. This makes it difficult to accurately control the bonding pressure during such a bonding operation.

Furthermore, with the conventional testing apparatus, the detection of a load applied to the test piece is effected by a load cell attached to the actuator which is used to lift the test piece, thereby to render difficult precise measurement of any pressure applied between the test pieces during the bonding operation while during the peeling operation, a load can be detected only when it reaches its peak value.

As described above, the test piece is fixedly secured at its one end by the clamp, and so the test pieces are easily subjected to deformation at the time of pressure contact as well as peeling. In order to avoid such inconveniences, use is made of a boxboard, plastic plate, metallic plate, etc., having a high flexural strength as a test piece. For this reason, the above mentioned test is considered to be less practical in case the hot-melt adhesive is used in adhesion of corrugated boards, and thus, any test result obtained is deemed less reliable.

SUMMARY OF THE INVENTION

For the purpose of resolution of said tasks, the present invention employs the following structural arrangement.

The testing apparatus for hot-melt adhesion strength in accordance with a first invention is adapted to measure the bonding strength of a hot-melt adhesive by pressing a first test piece with said hot-melt adhesive applied thereto on a second test piece for contact bonding therebetween, and separating the both test pieces after the passage of a determined period of time to detect a resultant tensile force, which apparatus comprises a movable actuator, as means for taking said second test piece away from its rest position to press it on said first test piece, for transferring with a relative high speed the second test piece closer to said first test piece, and a pressing actuator disposed in series relative to said movable actuator and adapted to convey the second test piece transported by the movable actuator from the rest position with a relatively slow speed so as to place the second test piece on the first test piece for further pressing.

The adhesion strength testing apparatus in accordance with a second invention is adapted to measure the adhesion strength of a hot-melt adhesive by pressing a first test piece with a hot melt adhesive applied thereto on a second test piece into close contact therewith, and separating the both test pieces after the passage of a determined period of time to detect a resultant tensile force, which apparatus includes a table for fixedly holding the first test piece supported by a load cell of cantilever beam type projecting from the machine frame so that a force applied to the first test piece may be detected by said load cell via the table.

The adhesion strength testing apparatus in accordance with a third invention is adapted to stick a test piece of corrugated board with a hot-melt adhesive applied thereto on another test piece of corrugated board and separating the both test pieces after the passage of a determined period of time to detect a resultant tensile force, and which apparatus includes a test piece holding member consisting of a plurality of parallel needles which have been inserted into the hollow portion between one surface and another of the test piece and common frame members for securing the ends of said needles.

In accordance with the adhesion strength testing apparatus of the first invention, a quick and highly accurate contact bonding can be achieved by moving the second test piece with the movable actuator close to a position where the contact bonding takes place and then pressing the second test piece on the first test piece by the use of the pressing actuator.

In accordance with the adhesion strength testing apparatus of the second invention, a precise measurement of a tensile force resulting from the peeling action can be performed successively by detecting a load by the load cell via the table which is supported by the load cell and on which the test pieces are fixed.

In accordance with the adhesion strength testing apparatus of the third invention, a test piece can be fixedly placed in position in the apparatus by inserting a plurality of needles from the side into the hollow portion of a corrugated board as test piece and securing the needles at their ends by means of the frame members. At this time, since the parallel needles are arranged in the form of a bone structure within the interior of the test piece, appropriate bonding pressure and peeling may be achieved to obtain a precise test result.

DETAILED DESCRIPTION OF THE INVENTION

Figure 1:
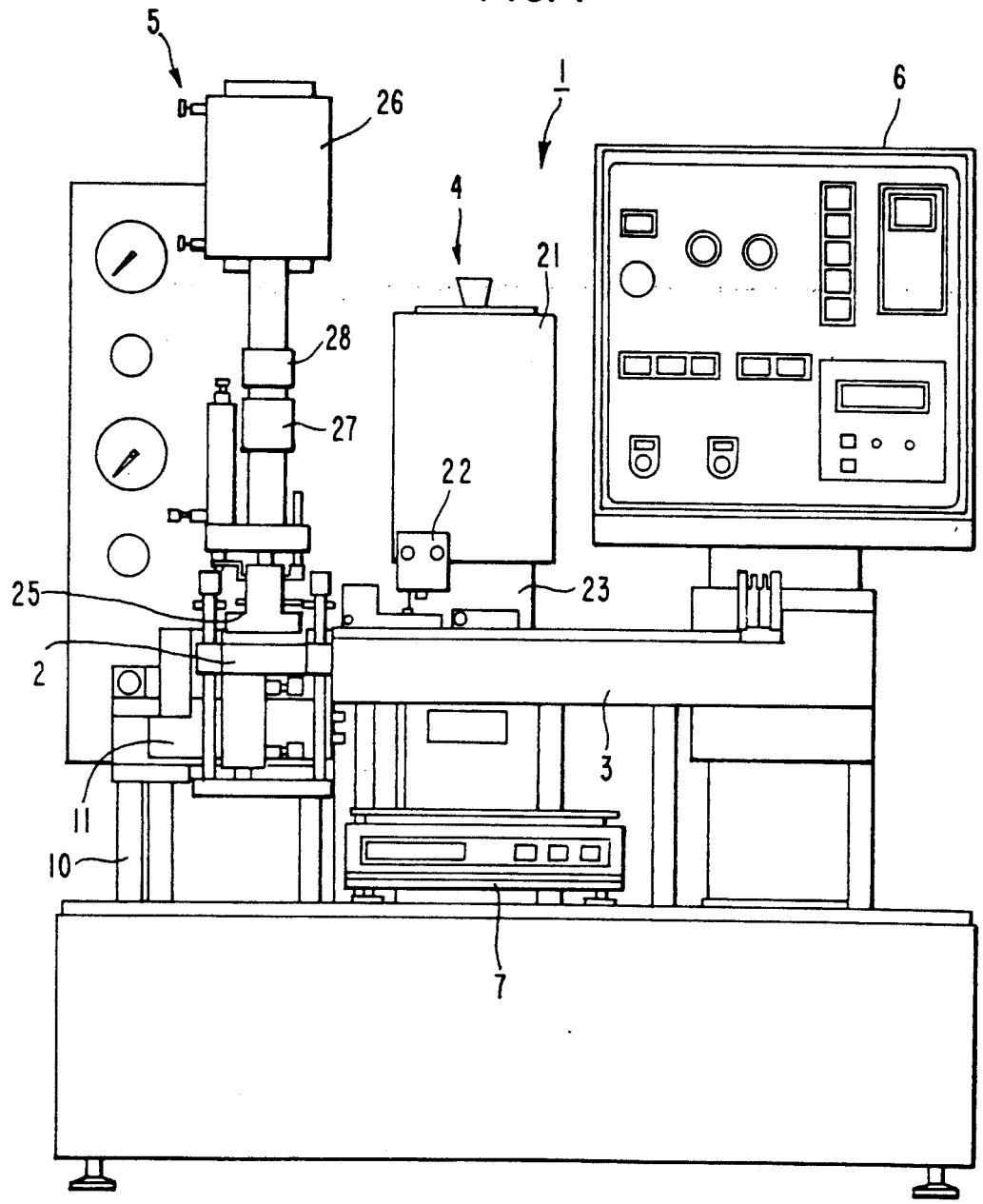
FIG. 1 is a front view of a first embodiment of the adhesion strength testing apparatus in accordance with the present invention.
Figure 2:
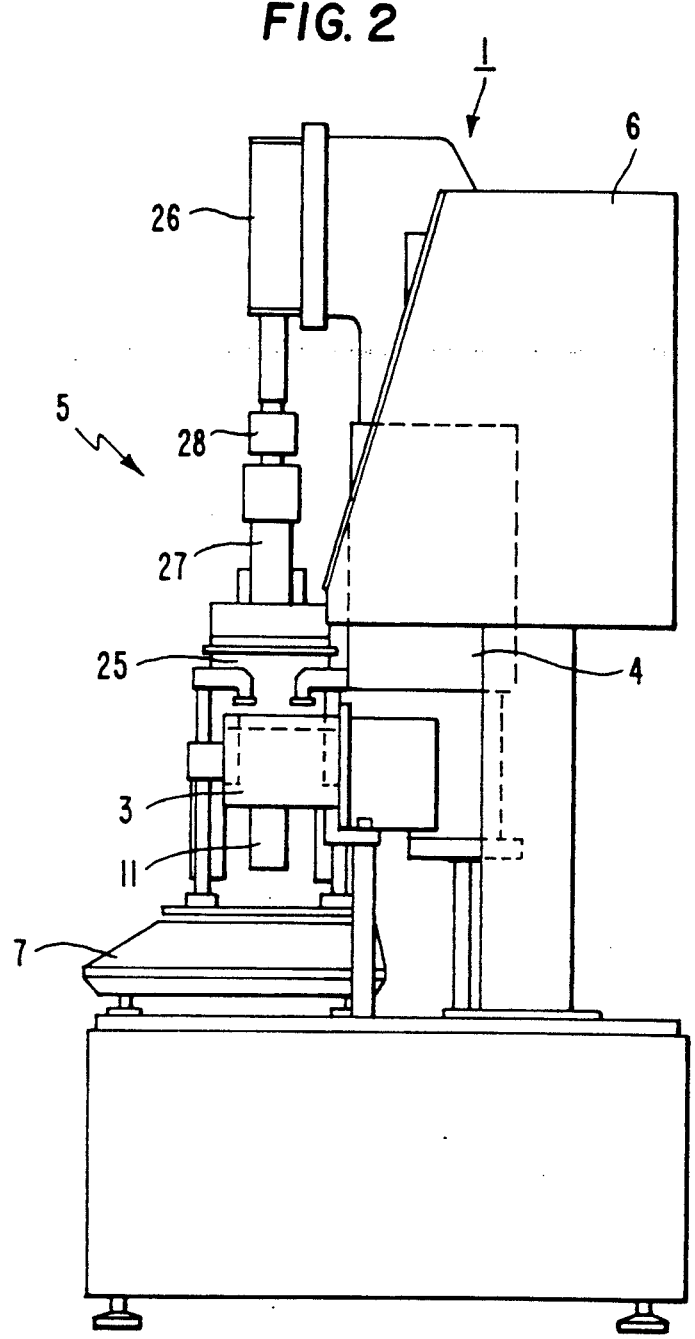
FIG. 2 is a side view of FIG. 1.
Figure 3:
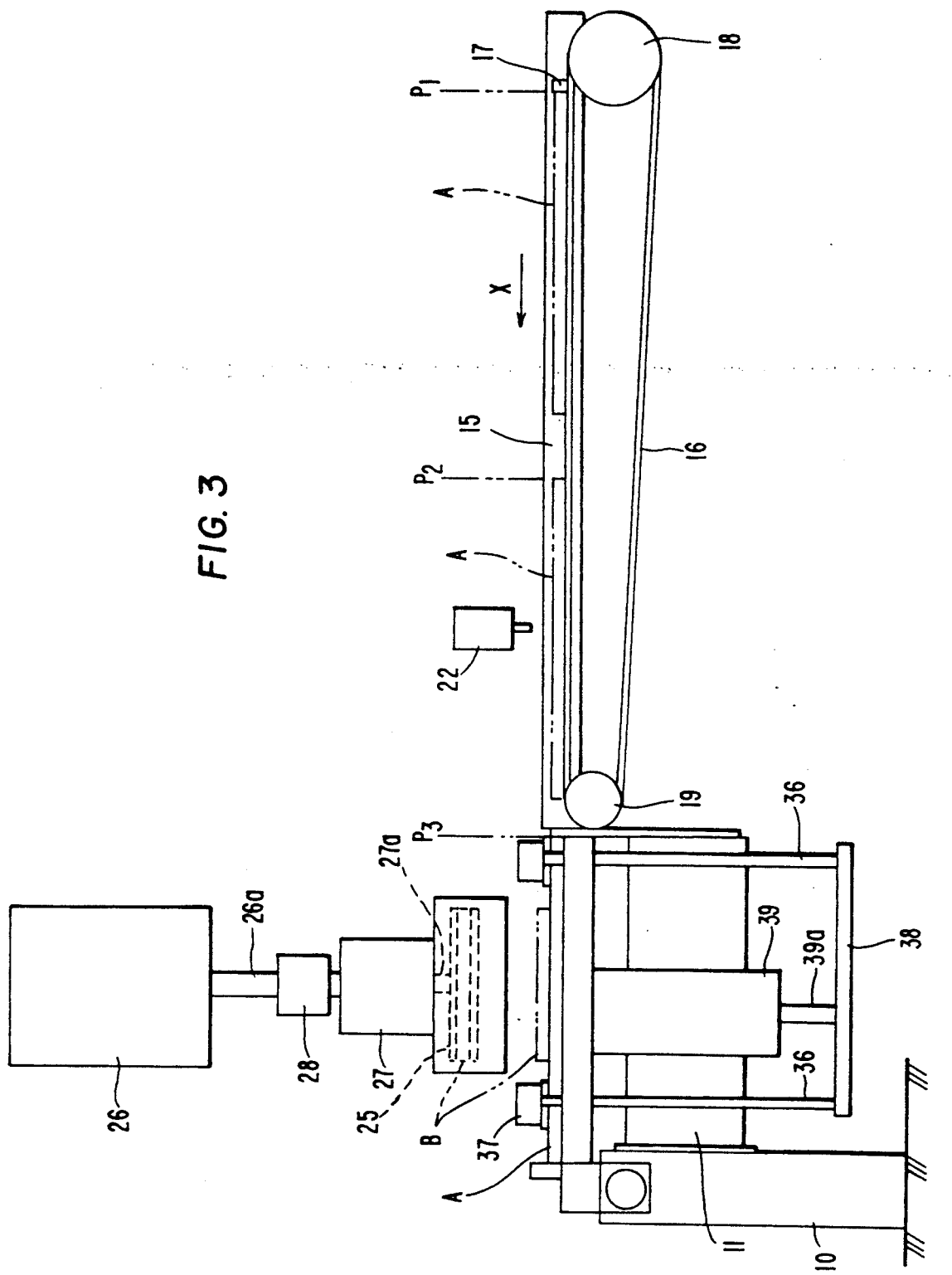
FIG. 3 is a front view showing substantial parts.
Figure 4:
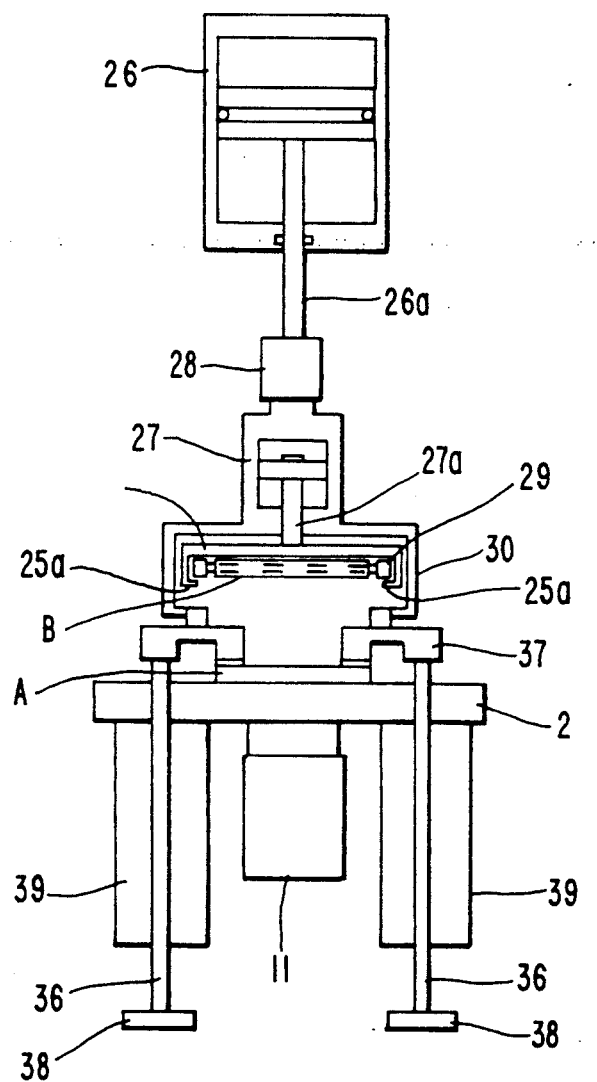
FIG. 4 is a side of FIG. 3.

FIGS. 1-4 illustrate one embodiment of the adhesion strength testing apparatus in accordance with the present invention. This particular adhesion strength testing apparatus 1 is intended to measure an adhesion strength resulting from a hot-melt adhesive with which two test pieces A, B are joined together. The apparatus comprises a clamp table 2, a transfer unit 3 for transferring a first test piece A along a determined passageway to said clamp table 2, an applicator unit 4 for applying an adhesive to the top face of the test piece A on said passageway, contact bonding/peeling unit 5 for pressing the second test piece B on the test piece A when the latter has reached said clamp table 2 on one hand and peeling the adhered test pieces A, B one from another on other hand, and a control unit 6 for controlling the respective units. Referring to FIGS. 3 and 4, the numeral 7 designates a balance for weighing hot-melt adhesives.

Figure 7A:
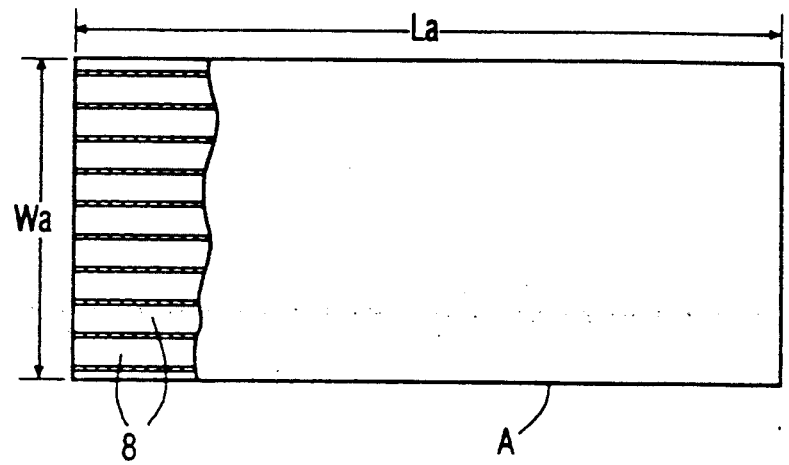
FIGS. 7A and 7B are plan views showing first and second test pieces respectively.
Figure 7B:
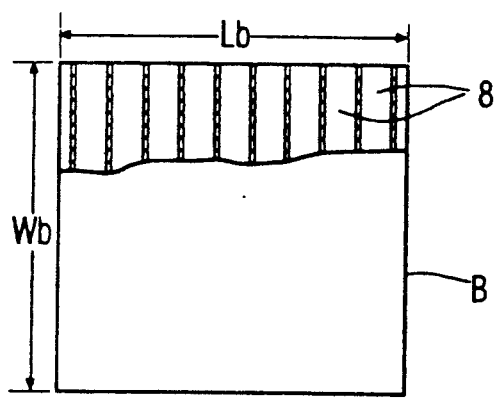

The illustrated test pieces A, B each are made of corrugated boards each consisting of a card board bent into a series of groves and ridges and flat paperboards stuck on the both faces of the corrugated card board respectively. As shown by FIG. 7, the both test pieces A, B are equal in width (Wa = Wb), and the test piece A is longer than the test piece B (Ld > Lb). The test piece A has elongated hollow portions 8 arranged to extend lengthwise, while the test piece B has hollow portions 8 arranged to extend widthwise.

The clamp table 2 is supported by a load cell 11 mounted on a machine frame 10 so as to form a cantilever beam.

The transfer unit 3 has a pair of guide rails 15, 15 provided with an interval therebetween above the clamp table 2, and a timing belt 16 provided in the space between the rails. The timing belt 16 has a hook projection 17 attached to a proper position thereon so that as said timing belt moves, the test piece A will be urged by the hook projection to move in an X direction. There are three different positions set on the transfer passageway, i.e. an original position P1 at one end, an adhesive applying position P2 at the intermediate point, and contact bonding position P3 at the other end existing on the clamp table 2. The timing belt 16 and a pair of pulleys 18, 19 over which the timing belt runs are provided with teeth having same pitches so that the toothed belt and pulleys may mesh with each other for transmission purpose to avoid any idling, thereby resulting in an accurate operation timing.

The adhesive applicator unit 4 has a hot-melt adhesive, a nozzle 22 provided above said adhesive applying position P2, and a discharge pump 23 for supplying the adhesives contained in the tank 21 to 22. The tank 21 includes a heater (not shown) which acts to keep the contained adhesive in a molten state at an adequate temperature. The discharge pump 23 is a gear pump with a high degree of accuracy which may reduce to the utmost variations of discharge rate due to variations of the adhesive in viscosity so that an exact amount of adhesives can be supplied to the test pieces.

The contact bonding/peeling unit 5 has a holder 25 located above said contact bonding position P3 for holding the test piece B, the holder being moved in a vertical direction by a vertically movable actuator 26 constituted by an air cylinder and a pressing actuator 27 for contact bonding purpose. The movable actuator 26 secured to the machine frame is mounted at the lower end of d rod 26a to the pressing actuator 27 via a joint 28. The holder 25 takes the form of spanning the clamp table 2, with grooves 29, 29 for attaching a test piece holding member 30 which will be described later to lower ends of perpendicular portions 25a, 25a. As illustrated, the movable actuator 26 has a large stroke and the pressing actuator has a small stroke, and in particular, the pressing actuator 27 uses an air cylinder with a high degree of accuracy, thus causing less mechanical loss in its seal portion.

Figure 5:
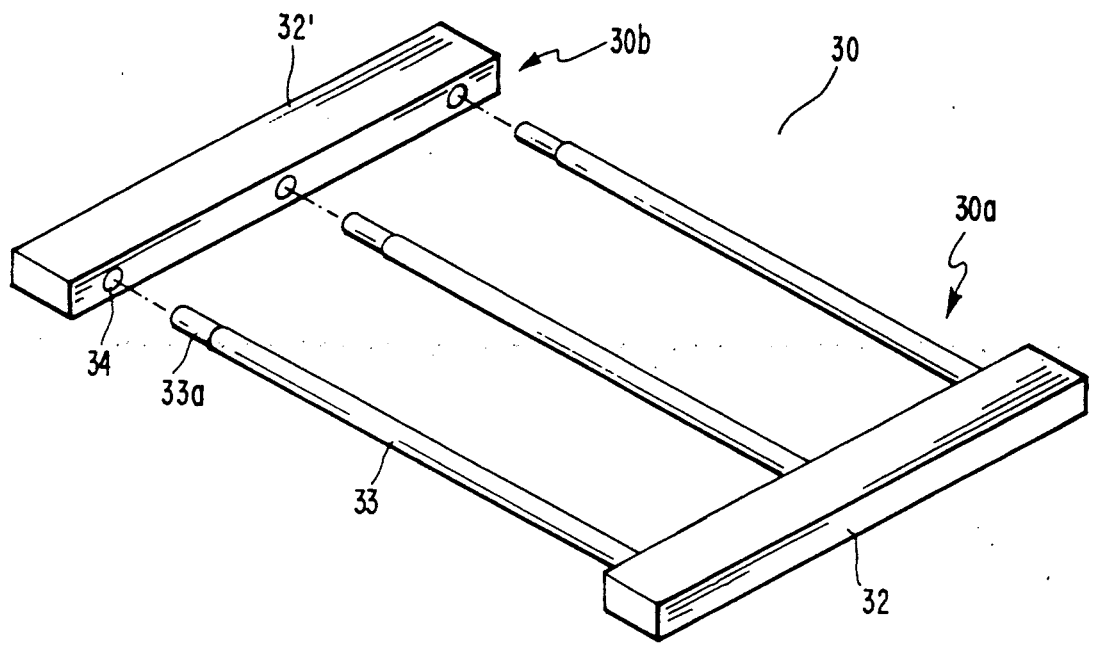
FIG. 5 is a perspective view of a test piece holding member.
Figure 6:
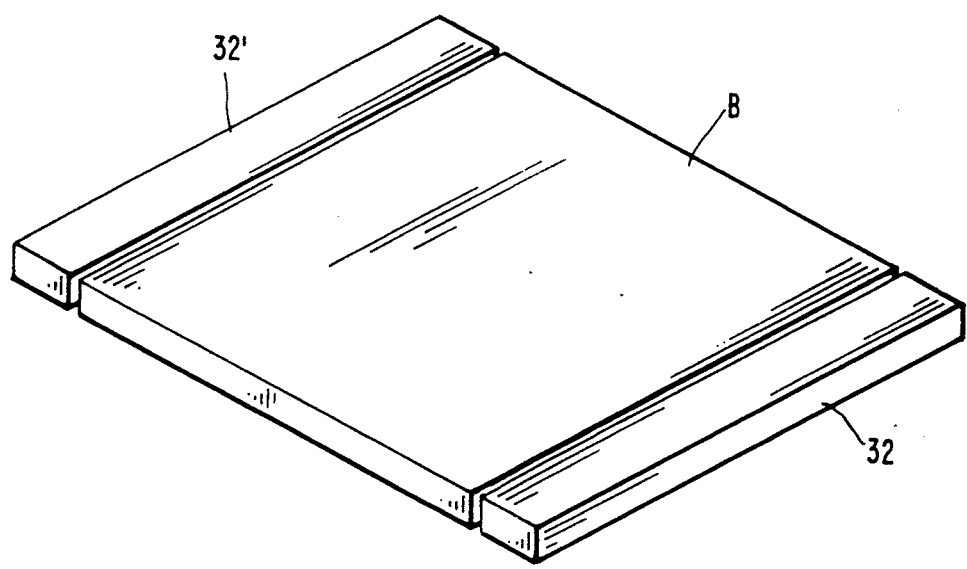
FIG. 6 is a perspective view of the test piece holding member in use.

The test piece holding member 30 as shown in FIG. 5 is used in attaching the test piece B to the holder 25. The test piece holding member 30 is constituted by a first member 30a having three parallel needles 33, . . . received by a frame member 32 and a second member 30b comprising a frame member 32, some as said frame member 32 having holes 34, . . . into which said needles 33, . . . are fit. The needles 33, of the first member 30 are penetrated from one side into the hollow portions 8, ... of a corrugated board as the second test piece B, and the top ends of the needles 33, . . . which have jutted out into the other side are fitted into the holes 34, . . . of the second member 30b to leave a combination of the test piece B and holding member (FIG. 6). The test piece B may be attached to the holder 25 by fitting the frame members 32, 32 of the combination into said grooves 29, 29.

If very strong card boards, plastic plates, metallic plates, etc. , are used as a test piece rather than corrugated boards, such a holding member is not necessary, and the test piece may be mounted directly to the holder.

There are provided above 4 corners of the contact bonding position P3 press members 37, ... supported by elevator rods 36, ... Two opposite rods 36, ... are coupled at the lower ends with a connecting frame 38, on which is mounted a piston rod 39a of an air actuator 39 provided below the clamp table 10. The movement of expansion and contraction of a pair of actuators 39, 39 positioned in parallel allows 4 press members 37, . . . to go up and down.

Next, the operations of the respective units under the control of the control unit 6 will be described.

Before a test starts, the test piece B is mounted on said holder 25, while the test piece A is set on the original position P1 of the transfer unit 3. The timing belt 16 is actuated to convey the test piece A toward the adhesive applying position P2, where the test piece A is coated with a predetermined amount of adhesives by means of the applicator unit 4. In this instance, there are two optional methods of application, i.e. the one is the "bead coating" in which the adhesive is applied to the moving test piece A, and the other method is the "spot coating" in which the test piece A is stopped temporarily to be coated with adhesives. Upon completion of the coating, the test piece A is transmitted toward the contact bonding position P3.

After a lapse of time, further operation starts with expansion of the movable actuator 26, causing the test piece B to go downward until it is brought in contact with the test piece A, with the consequential expansion of the pressing actuator 27 so as to press the test piece B on the test piece A. Such a bonding contact can be positively secured because the test piece B is supported in a two-dimensional manner by 3 needles 33, . . . received by the hollow portions 8, . . . As the both test pieces are positioned in such a manner that the hollow portions of the test pieces cross each other in the bearings, the test pieces will become less deformed, if any, when the pressure contact takes place. The pressing force applied at the time of contact is detected by the load cell 11 via the clamp table 2. The time during which the test pieces A and B are joined together after the test piece A has been coated with adhesives is called the "open time". This open time may be set at discretion, e.g. based on 0.1 second. In case of "bead coating", the open time can be set ranging from 0.4 to 100 seconds, and in case of "spot coating", 0.6–100 seconds. In a determined period of time after the both test pieces have been adhered to each other under pressure, the pressing actuator 27 is contracted to release the acting pressure. The time in which to apply pressure can be optionally set. The execution of elevation and contact bonding by the two actuators 26, 27 at two dividing stages may ensure a quick elevation mode and a fine adjustment of the pressure. In addition, the detection by the load cell 11 of the pressure permits a highly accurate control of the pressure.

In a given period of time after the two test pieces A, B have been brought in close contact with each other, the pressing members 37, ... are lowered to abut against the four corners of the test piece A, so as to press the latter onto the surface of the clamp table, and then, the test piece B is raised by the subsequent contraction of the movable actuator 26 until the adhesive joint between the both test pieces is started. At this moment, the load cell 11 acts to detect a tensile force applied to the clamp table 2. The test piece B will never bend with the support of the needles 33, ... attached to the test piece. The time during which the both test pieces are peeled from each other after their joining is called the 'set time', and this also may be set at discretion based on 0.1 second. This set time is usually set in the order of 0.1–100 seconds. The time in which to lift the test piece B by the use of the movable actuator 26 can also be set on step-by-step basis.

As described above, in accordance with the adhesive strength testing apparatus of the present invention, since the movement of the two test pieces by the movable actuator toward each other is done independently from the close contact of the two test pieces by the pressing actuator with each other, a quick operation for bringing the test pieces into close contact with each can be ensured and a fine adjustment of pressure is made possible as well and thus, this enables an efficient and highly accurate test.

The detection of a load applied to a test piece using the load cell via the table on which the test piece is fixed and which is supported by the load cell in the shape of a cantilever beam may simplify the structure of the apparatus and realize a highly accurate measurement of pressure and tensile force.

Furthermore, if a corrugated board is used as a test piece, it is retained by a plurality of needles inserted into the hollow portions of the corrugated board. This may ensure the easy and secured maintenance of the corrugated board test piece. Therefore,, in the adhesion strength test for adhesive, the contact bonding and peeling can be properly effected, and the test piece used is hard of deformation, thereby enabling a highly accurate test.

What is claimed is:

1. A hot-melt adhesion strength testing apparatus for measuring the bonding strength of a hot-melt adhesive by pressing a first test piece with said hot-melt adhesive applied thereto on a second test piece for contact bonding therebetween, and separating both test pieces after the passage of a predetermined period of time to detect a resultant tensile force, characterized in that the apparatus comprises a table supported by a load cell of cantilever beam type, a first actuator for transferring the second test piece from its first position closer to said first test piece fixedly positioned on the table, and a pressing actuator adapted to convey the second test piece transported by the first actuator from the second position so as to place the second test piece on the first test piece for pressing, said first actuator also serving as a means for separating the second testpiece from the first test piece after pressing with a presser actuator for a predetermined period of time, the load cell being capable of detecting the amount of tensile force applied to the first test piece.

2. The apparatus of claim 1 wherein the apparatus further comprises a test piece holding member consisting of a plurality of needles which have been inserted in the hollow portions between one surface and another of the first test piece and common frame members for securing the ends of said needles.

* * * * *